United States Patent [19]

Siebel et al.

[11] Patent Number: 4,912,332
[45] Date of Patent: Mar. 27, 1990

[54] NON-DESTRUCTIVE METHODS FOR DETECTING ORGANIC DEPOSITS AND REMOVING THEM

[75] Inventors: Maarten A. Siebel, Bandung, Indonesia; William G. Characklis, Bozeman, Mont.; Rune Bakke, Stavanger, Norway

[73] Assignee: Research and Development Institute, Inc. at Montana State University, Bozeman, Mont.

[21] Appl. No.: 201,994

[22] Filed: Jun. 3, 1988

[51] Int. Cl.⁴ .................. G01F 23/28; G01N 21/59
[52] U.S. Cl. .................. 250/356.1; 250/341; 250/373; 250/431
[58] Field of Search ............ 250/356.1, 341, 358.1, 250/359.1, 373, 431, 432 R

[56] References Cited

U.S. PATENT DOCUMENTS

| | | | |
|---|---|---|---|
| 2,660,678 | 11/1953 | Sigworth et al. | 250/358.1 |
| 2,957,987 | 10/1960 | Arnesen | 250/358.1 |
| 3,281,597 | 10/1966 | Greenberg | 250/351 |
| 3,544,798 | 12/1970 | Topol | 250/573 |
| 3,557,376 | 1/1971 | Senyk | 250/573 |
| 3,864,044 | 2/1975 | Lyshkow | 250/573 |
| 3,872,310 | 3/1975 | Charlton et al. | 250/358.1 |
| 3,919,702 | 11/1975 | Hayes et al. | 250/573 |
| 4,034,219 | 7/1977 | Louden et al. | 250/431 |
| 4,371,786 | 2/1983 | Kramer | 250/343 |
| 4,429,225 | 1/1984 | Fumoto et al. | 250/353 |
| 4,490,612 | 12/1984 | Törmälä | 250/341 |
| 4,543,482 | 9/1985 | Brenholdt | 250/343 |
| 4,574,387 | 3/1986 | Gignoux et al. | 250/358.1 |
| 4,631,408 | 12/1986 | Zelmanovic et al. | 250/341 |
| 4,631,529 | 12/1986 | Zeitz | 250/573 |
| 4,695,729 | 9/1987 | Monno et al. | 250/359.1 |

Primary Examiner—Constantine Hannaher
Attorney, Agent, or Firm—Lowe, Price, LeBlanc, Becker & Shur

[57] ABSTRACT

A non-destructive method for the early detection of the formation of organic deposits or a biofilm on the internal surface of a conduit through which a fluid passes comprises allowing the fluid to flow through a conduit, passing a light beam, e.g., IR or UV light, through the fluid and the deposits in a direction transversal to the surface thereof, detecting and measuring the transmitted portion of the light beam after it has emerged from the fluid and the deposits, conducting these measurements at least twice at a set time interval, the first time before any materials deposit, and calculating % variation absorbed light during the time interval, which value is proportional to the organic materials or biofilm deposited and a method of removing at least a portion of organic deposits or a biofilm deposited on the internal surface of a conduit through which a fluid flows comprises allowing the fluid to flow through a conduit having a deposited organic layer or biofilm, passing a light beam, e.g., IR or UV light, through the fluid and the deposited material in a direction transversal to the surface thereof, detecting and measuring the transmitted portion of the light beam after emerging from the fluid and the deposits, and adding deposit removing means to the flowing fluid to remove at least a portion of the organic deposit or biofilm.

17 Claims, 4 Drawing Sheets

NON-DESTRUCTIVE METHODS FOR DETECTING ORGANIC DEPOSITS AND REMOVING THEM

BACKGROUND OF THE INVENTION

1. Technical Field

This invention relates to a non-destructive method for the early detection of organic materials deposited on the internal surface of a conduit through which fluid flows in a continuous or semi-continuous manner. This invention also relates to a method of removing at least a portion of the organic deposit. The present methods are useful for the early detection of the formation and the removal of undesirable deposits of organic, biological or biochemical materials on the internal surfaces of reactors and pipelines subjected to continuous or semi-continuous flows. Examples of these are industrial plant reactors, water pipelines, oil pipelines, power plant condensers and the like.

2. Background Art

Biofilms are organic slime layers consisting of microbial and higher life forms held together by an inorganic and/or organic matrix. However, biofilms may contain other chemical compounds and particulate materials in addition thereto. Biofilms form in aqueous environments by deposition of biological and other materials on the internal surfaces of containers, conduits and the like.

In many instances, biofilms can have a positive influence on the overlaying water quality, particularly in terms of suspended and dissolved materials contained therein. For this reason, biofilms may be an asset in both natural systems such as streams and lakes, and in engineering systems such as fixed-film biological waste water treatment plants and the like.

On the other hand, in most engineered systems biofilms are considered a nuisance which results at times in energy losses (in fluid flow systems), reduction of cooling capacity (heat-exchangers), enhancement of corrosion potential (oil pipelines), danger to public health (drinking water supplies) and the like. Therefore, the formation of biofilms must be closely monitored in order to prevent the occurrence of extreme conditions. Biofilm monitors now in use in general measure one of the above negative effects and signal when some preset value is reached. However, since the variable which is monitored is some undesirable effect, in order to become detectable, the value of such variable may already be in the undesirable range.

Accordingly, there is still a need for early monitoring and control of biofilms and methods of detecting their formation and the removal of at least a portion of the biofilm in an as early as possible stage, particularly before levels of undesirable effects are reached.

DISCLOSURE OF THE INVENTION

This invention relates to a non-destructive method for the early detection of organic materials or a biofilm being deposited on the internal surface of a conduit through which a fluid is allowed to flow in a continuous or semi-continuous manner, said method comprising (a) allowing a fluid to flow in a conduit in a continuous or semi-continuous manner;

(b) passing a light beam through said fluid and said organic materials in a direction transversal to the surface onto which the biofilm or materials are to deposit; said light beam having a wavelength in a range in which said organic materials absorb;

(c) detecting and measuring the transmitted portion $B_n$ of said light beam after it has emerged from said fluid and said organic materials at a time $n_i$, wherein $i = 0$;

(d) repeating steps (b) and (c) at a predetermined time interval, wherein $i = i + 1$ (e) calculating the % variation light transmitted during said time interval from the formula $(Bn_i - Bn_o) \times 100 = \%$ Variation Absorbed Light $(n_o; n_i)$ said % Variation value being proportional to the variation in the amount of organic materials or biofilm deposited on the internal surface of said conduit during said time interval.

This invention also relates to a method of monitoring the removal of at least a portion of organic materials or a biofilm deposited on the internal surface of a conduit through which a fluid is allowed to flow in a continuous or semi-continuous manner, said method comprising (a) allowing a fluid to flow in a continuous or semi-continuous manner in a conduit having organic materials or a biofilm deposited on the internal surface thereof;

(b) passing a light beam through said fluid and said organic materials or biofilm in a direction transversal to the surface onto which the materials have deposited; said light beam having a wavelength in the range in which said organic materials absorb;

(c) detecting and measuring the transmitted portion $B_n$ of said light beam after it has emerged from said fluid and said biofilm or organic materials;

(d) calculating the % variation transmitted light from the formula $B_o - B_n) \times 100 = \%$ Variation Absorbed Light (n;o);

wherein $B_o$ is the value obtained by conducting steps (a) through (c) in the absence of deposits and said % Variation is proportional to the amount or organic materials or biofilm deposited; and if said % Variation reaches a preset value;

(e) applying a chemical or physical method to said flowing fluid to remove at least a portion of said organic materials or biofilm.

A more complete appreciation of the invention and many of the advantages thereof will be readily perceived as the same becomes better understood by reference to the following description when considered in connection with the accompanying Figures.

Other objects, advantages and features of the present invention will become apparent to those skilled in the art from the following discussion.

BEST MODE FOR CARRYING OUT THE INVENTION

The present invention arose from the desire of the inventors to improve over existing methods for monitoring and controlling biofilm and organic materials deposition, and particularly to provide a means for early detection and removal of biofilms before they bring about undesirable results in the systems where they are deposited.

The methods described in this invention use an analytical technique called spectrometry, and preferably infrared (IR) and ultraviolet (UV) spectrometry, for detecting qualitative and/or quantitative changes in chemical compounds contained within matrices of sediments, silt, inorganic precipitates, corrosion products and the like, to be monitored. Examples of these compounds are organic and biochemical compounds which are embedded in the deposits and/or attached to inorganic, biological or biochemical materials such as cells or proteins also embedded in the biofilms. These organic compounds may also be produced by the biological or chemical materials found in the deposits or biofilm. To that extent their detection is a clear indication of the extent of the presence of such inorganic, biological or biochemical materials in the deposits or biofilm.

Devices or apparatus for practicing the present methods are based on extremely simple principles and can be easily built into existing systems such as water mains, reactors, reactor pipelines and the like. These devices or apparatus permit the continuous non-destructive monitoring of an organic deposit or biofilm and can be fully automated. The apparatus for implementing the methods of the invention can be mounted in situ without interfering with biological or other processes being conducted in a system.

The present methods are based on the principle that biochemical and organic compounds are capable of absorbing light radiation of specific wave lengths, particularly infrared (IR) and ultraviolet (UV) lights. Different functional groups present in chemical compounds have specific wave length areas in which they are capable of absorbing light. Thus, specific "peaks" appear in the spectra which are characteristic of particular functional groups. In the case of infrared (IR) light, a compound will have a characteristic spectrum, from which can be found out which functional groups it contains. Conversely, knowing which groups a compound carries, the wave lengths for absorption can be obtained.

Moreover, the amount of light absorbed by a compound at a specific wavelength can be correlated with the mass of the compound in the light path. Accordingly, light absorption can be correlated with organic sediment or biofilm mass.

Figure 1:
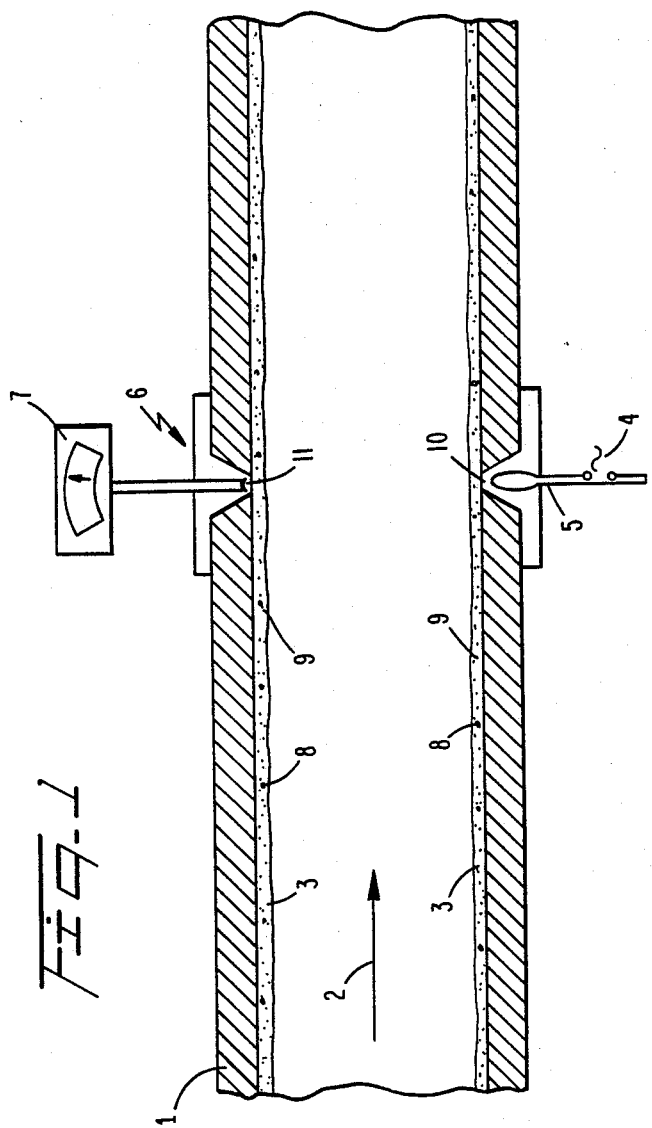
FIG. 1 is a diagram of a biofilm detecting device or apparatus utilized for practicing the methods of the invention. Shown in FIG. 1 are a conduit 1 through which a fluid 2 flows in the longitudinal direction thereof depositing a biofilm 3 comprising biological material such a cells 8 and chemical compounds 9. A power supply 4 is attached to a light emitter 5 at a point 10 of the conduit 1. Opposite point 10 of the conduit 1, at a point 11 of the conduit, is placed a light sensor 6 which is connected to a meter 7. When the power supply 4 is started, the light emitter 5 emits infrared (IR) light in a direction transversal to the flow of the fluid 2. This infrared light beam passes through the biofilm 3 and the fluid 2 before it reaches the light sensor 6 at the point 11 of conduit 1. The meter 7 reflects the amount of infrared light transmitted which has not been absorbed upon passage through the biofilm 3 and the fluid 2.

A device or apparatus useful for practicing the methods of the invention is schematically shown in FIG. 1. The fluid is transported longitudinally in a conduit. With the passing of time, organic materials or a biofilm deposits on the internal surfaces of the conduit. A light emitter is placed in an opening on the conduit wall pointing towards the inside of the conduit and is connected to a power supply. A light sensor is also placed in an opening on the opposite side of the conduit also pointing towards the conduit and is connected to a meter which reads the current generated in the sensor.

Upon accumulation of organic deposits or biofilm material or increase of the thickness of the biofilm, the amount of light absorbed will be increased and therefore the amount of light transmitted will be reduced. This will result in a reduction of the current circulating from the sensor to the meter.

In a particular embodiment of the invention, the first determination of the amount of light transmitted and detected by the sensor is obtained in the absence of any deposited organic materials or biofilm on the internal surface of the conduit. This can be taken as a value corresponding to "100%" transmission. Accordingly, any subsequent measurements can be related to this value by the formulas given herein. What is obtained is then an absolute % of transmitted or absorbed light at a particular point in time. This embodiment permits the monitoring of the formation of a biofilm and an early, non-invasive detection of this event.

Although the methods of the invention can be practiced under a variety of conditions, they yield best results when the fluid through which the infrared light beam is passed is substantially transparent to such rays. However, if the fluid is not totally transparent the present methods can still be practiced and the absorbance and/or transmittance values can be corrected as indicated above by taking a first measurement for the fluid in the conduit in the absence of organic sediments or biofilm.

In one embodiment, the methods of the invention are preferably practiced by utilizing infrared (IR) light beams having a wave length of about 810 nm to 920 nm, and more preferably 870 nm to 900 nm. A most preferred range of wave lengths is about 880 nm to 890 nm. However, other types of light beams may also be utilized at wave lengths where the chemical compounds absorb energy. One such type of light is ultraviolet (UV) light of various wavelengths.

In another preferred embodiment of the invention, where a qualitative measure of the biofilm is desired, the methods of the invention may be practiced by passing a light beam, preferably an IR light beam, through the fluid having at least one specified wavelength. The wavelengths are narrowly tailored for the detection of one or more specific functional group(s) present in a biochemical or organic compound known to be present in the organic deposits or biofilm. Thus, when a set of wavelengths closely associated with at least one functional group of a compound present in the organic deposits or biofilm is passed through the fluid, the measurements read in the meter can be directly correlated with the mass of that species or compound present in the biofilm. Accordingly, the measurements reflect the presence of organic, biological or biochemical materials which are producing such compound.

Wavelengths associated with different functional groups such as carbonyl, carboxyl, amine, amide, thiol, thionyl and the like, are known in the art and need not be listed herein. The measurements can be taken separately at different wavelengths and a set of redundant results can be arranged thereafter in another preferred embodiment. The necessary information on the correlation of functional groups and wave lengths of absorption bands is known in the art (e.g., Infrared and Raman Spectroscopy, Grasselli, J. G., Brame, E. G., Ed., Marcel Dekker (1977); Silverstein, Bassler and Morrill, Spectrometric Identification of Organic Compounds).

In a further embodiment of the invention a person with ordinary skill in the art may compile a Table of corresponding values of % Variation Absorbed Light and amounts of organic deposits or biofilm obtained for a particular fluid flowing in a particular conduit in a particular system. By resorting to such Table any measurement of the meter or a % Variation Absorbed Light monitoring progress of deposit of organic materials or biofilm) or % Increase Transmitted Light (Removal of biofilm) calculated therefrom can be correlated with the amount of the organic deposits or biofilm deposited on the internal surface of the conduit.

These calculations can be fully automated and the Table of corresponding values stored in a computer memory. In practice, a continuously monitored system will permit a very early detection of the formation of the organic deposits or biofilm.

Moreover, in another embodiment of the invention when a preset thickness is attained a signal may be elicited to trigger the addition of a deposits removing means to the fluid to promote the removal of at least a portion of the organic deposits or biofilm.

In this context, a deposits removing means is understood to be a chemical or other means of removing or inactivating organic, biological or biochemical materials forming a biofilm along with a matrix in which they are embedded. In the case of biological materials such as cells from microbial or higher organisms the removing means may be a chemical such as chlorine, an antibiotic or other chemical compound lethal to the cells. In the case of the organic or biochemical materials the removing means may be a pH change promoter such as an acid or an alkaline compound, a compound capable of irreversibly binding with a protein and/or enzyme and the like. Mechanical means such as particulate material may also be added to the fluid to aid in the mechanical removal of the organic deposits or biofilm as well as the embedding matrix.

Having now generally described this invention, the same will be better understood by reference to certain specific examples, which are included herein for purposes of illustration only and are not intended to be limiting of the invention or any embodiment thereof, unless so specified.

EXAMPLES

Example 1

Figure 2:
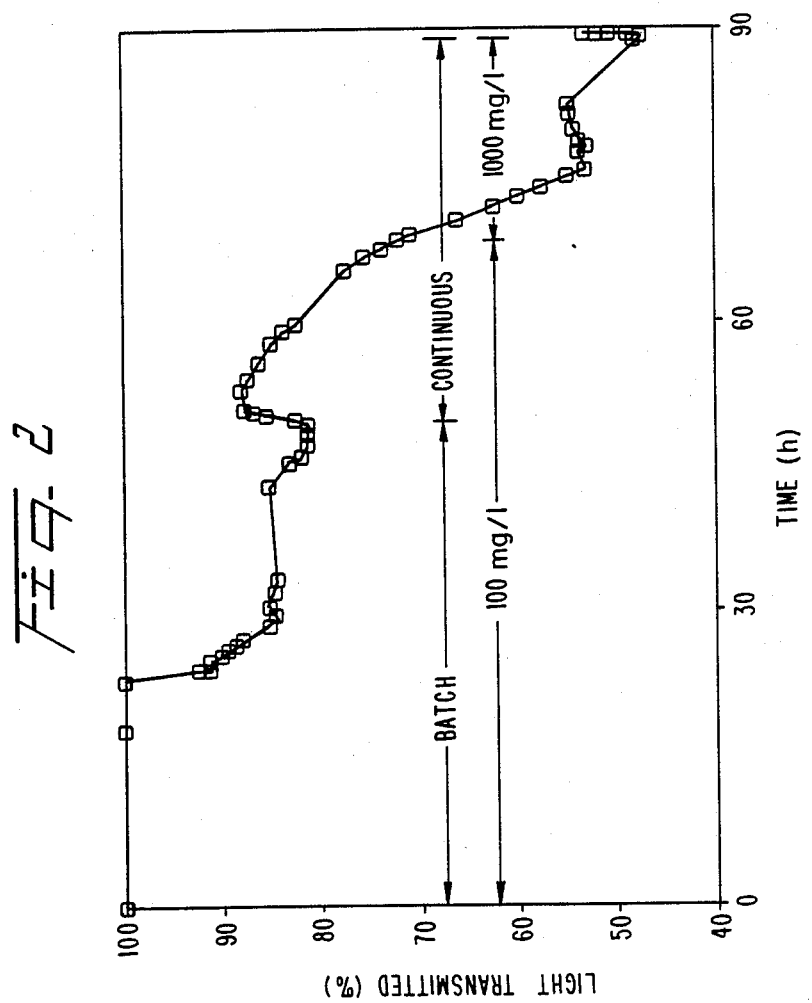
FIG. 2 shows a graphical representation of the % IR light transmitted as a function of time by the reactor utilized in Example 1 during monitoring of the formation of a biofilm.

Early non-destructive detection of the formation of an organic deposit or biofilm A reactor customarily used to study biofilm processes is used to follow the formation of a biofilm under different operational conditions while continuously measuring infrared (IR) light transmission. The results of the infrared (IR) light transmission measurements are shown in FIG. 2.

For the first 50 hours the reactor is operated in a batch mode where there is no flow of fluid in or out of the reactor. The fluid initially contains about 100 mg glucose/1. The composition of the fluid is maintained constant in order not to interfere with the transmission of infrared light. Subsequently, glucose is fed 100 mg glucose/1 at a flow rate of 2.5 ml/min for 35 hours. The infrared light transmitted is continuously monitored throughout the process. At the end of this period a visible biofilm develops. The transmission of infrared light at this point is reduced to about 50% of its initial value as can be seen in FIG. 2.

Example 2

Removal of a portion of a deposited organic biofilm

Figure 3:
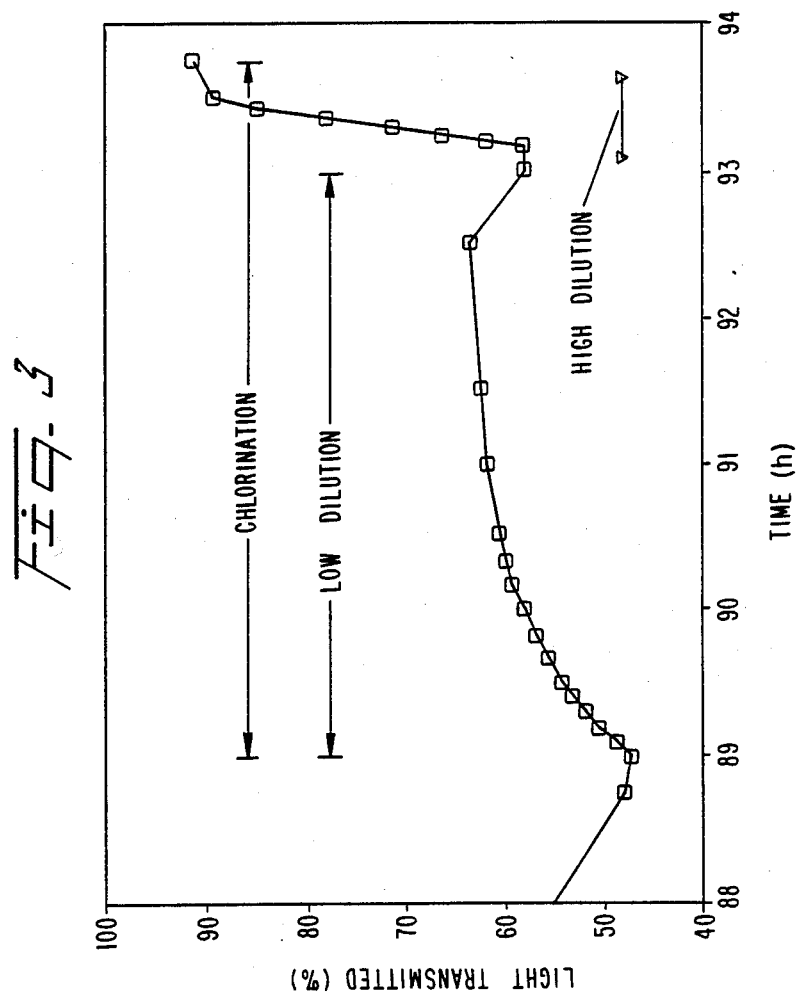
FIG. 3 shows the % IR light transmitted as a function of time in a reactor utilized in Example 2 for the removal of a biofilm.
Figure 4:
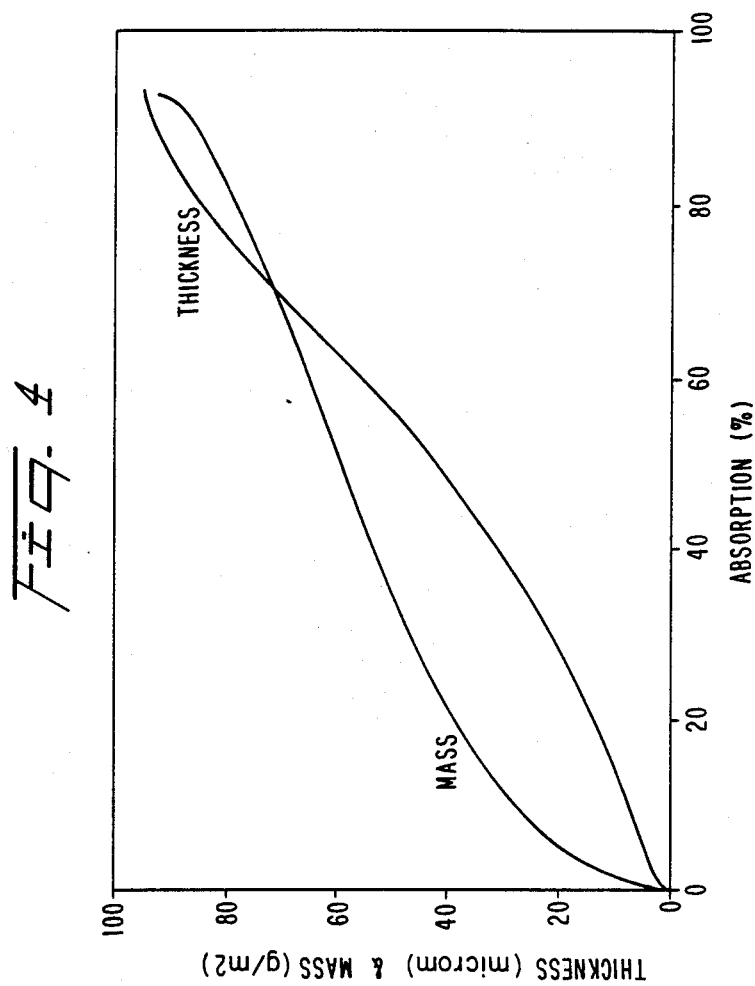
FIG. 4 is a graph representing the thickness and mass of a biofilm and their corresponding % light absorption.

The biofilm formed in Example 1 is removed by continuously feeding 10 mg chlorine/1 at a rate of 2.5 ml/min. The results of this test are shown in FIG. 3.

The % Infrared Light Transmission increases rapidly between 89 and 92.5 hours. However at this point the removed biological material starts to accumulate in the fluid which moves at substantially low flow rate though the reactor. Thereafter there is a slight decrease in the % Infrared Light being transmitted.

At 93 hours after the initiation of the process, the flow of the water fluid into the reactor is increased to 1000 ml/min in order to more rapidly remove the suspended material. Thereafter, the % Infrared Light Transmitted increases dramatically to reach about 90% of the initial value.

The invention now being fully described, it will be apparent to one of ordinary skill in the art that many changes and modifications can be made thereto without departing from this experiment or scope of the invention as set forth herein.

We claim:

1. A non-destructive method for the early detection of organic materials being deposited on the internal surface of a conduit through which a fluid is allowed to flow, said method comprising:
   (a) allowing a fluid to flow in a conduit;
   (b) passing a light beam through said fluid in a direction transversal to the surface onto which the materials are to deposit; said light beam having a wave length in a range in which said organic materials absorb;
   (c) detecting and measuring the transmitted portion $B_{ni}$ of said light beam after it has emerged from said fluid and said organic materials at a time $n_i$, wherein $i=0$;
   (d) repeating steps (b) and (c) at a predefined time, wherein $i=i+1$; and
   (e) calculating the % variation light absorbed during said time interval from the formula
   $(B_{ni}-B_{no})\times 100=\%$ Variation Absorbed Light $(n_i;n_o)$ said % Variation value being proportional to the variation in the amount of organic materials or biofilm deposited on the internal surface of said conduit during said time interval.

2. The method of claim 1, wherein
the light beam is an infrared (IR) light beam.

3. The method of claim 2, wherein
said IR light beam has a wave length of about 810 to 920 nm.

4. The method of claim 2, wherein
the light beam is an IR light beam; and
the wave length of said IR light beam is comprised of a narrow range of wavelengths associated with at least one functional group of at least one compound present in the biofilm.

5. The method of claim 1, wherein
the light beam is an ultraviolet (UV) light beam.

6. The method of claim 1, wherein
$B_o$ is detected and measured in the absence of an organic deposit or biofilm; and
the % Variation Absorbed Light indicates the % Increase Absorbed Light results from the formation said deposit or biofilm.

7. The method of claim 1, wherein
said fluid is substantially light transparent.

8. The method of claim 1, wherein
the fluid is allowed to flow in a continuous or semi-continuous manner.

9. A method of removing at least a portion of organic materials or a biofilm deposited on the internal surface of a conduit through which a fluid is allowed to flow, said method comprising
(a) allowing a fluid to flow in a conduit having organic materials or a biofilm deposited on the internal surface thereof;
(b) passing a light beam through said fluid in a direction transversal to the surface onto which the materials or biofilm have deposited, the light beam having a wave length in a range in which said organic materials absorb;
(c) detecting and measuring the transmitted portion $B_n$ of said light beam after it has emerged from said fluid and said organic materials or biofilm;
(d) calculating the % Variation Light Absorbed from the formula
$(B_o - B_n) \times 100 = \%$ Variation Absorbed Light (n;o);
wherein $B_o$ is the value obtained if steps (a) through (c) are conducted in the absence of deposits and said % Variation value is proportional to the amount of organic materials or biofilm deposited; and if the % Variation reaches a preset value
(e) adding a deposit removing means to said flowing fluid at a specified flow rate to remove at least a portion of the organic materials or biofilm.

10. The method of claim 9, wherein
the light beam is an IR light beam.

11. The method of claim 10, wherein
the wave length of the IR light beam is comprised of a narrow range of wavelengths associated with at least one functional group in at least one compound present in the biofilm.

12. The method of claim 10, wherein
the IR beam has a wavelength of about 810 to 920 nm.

13. The method of claim 9, wherein
the light beam is an IR light beam; and
the wavelength of the IR light beam is comprised of a narrow range of wavelengths associated with at least one functional group of at least one compound present in the biofilm.

14. The method of claim 9, wherein
the light beam is an ultraviolet (UV) light beam.

15. The method of claim 9, wherein
the fluid is allowed to flow at a higher flow rate in step (e) than in step (a) to obtain a high rate of removal of at least a portion of the biofilm.

16. The method of claim 9, wherein
the means added to step (e) comprises chlorine.

17. The method of claim 9, wherein
the fluid is allowed to flow in a continuous or semi-continuous manner.

* * * * *